United States Patent [19]

Garbe

[11] 4,296,758

[45] Oct. 27, 1981

[54] SPIROMETERS

[76] Inventor: Dietmar R. Garbe, Maids Moreton House, Maids Moreton, Buckingham, England

[21] Appl. No.: 85,273

[22] Filed: Oct. 16, 1979

[30] Foreign Application Priority Data

Oct. 16, 1978 [GB] United Kingdom ............ 40690/78
Jan. 25, 1979 [GB] United Kingdom ............ 02625/79

[51] Int. Cl.³ .............................................. A61B 5/08
[52] U.S. Cl. ...................................... 128/728; 346/72
[58] Field of Search ....................... 128/728, 725, 727; 346/33 ME, 72; 272/99

[56] References Cited

U.S. PATENT DOCUMENTS

| 2,999,495 | 9/1961 | Shipley | 128/728 |
| 3,086,515 | 4/1963 | Jones | 128/728 |
| 3,363,260 | 1/1968 | Garbe | 128/728 |
| 3,653,374 | 4/1972 | Talonn et al. | 128/728 |

Primary Examiner—Lee S. Cohen
Attorney, Agent, or Firm—A. W. Breiner

[57] ABSTRACT

A spirometer having an inflatable bellows 2, is provided with a movable member 15 which runs along a track 16. By adjusting parts 17, the configuration of the track is set locally to give a variable resistance to movement of member 15 and, consequently, inflation of the bellows 2. Calibration is achieved in a simple manner by adjusting parts 17 as the bellows is inflated progressively with measured amounts of air. Adjustments made correctly are not upset by adjustments made later in the calibration operation.

13 Claims, 5 Drawing Figures

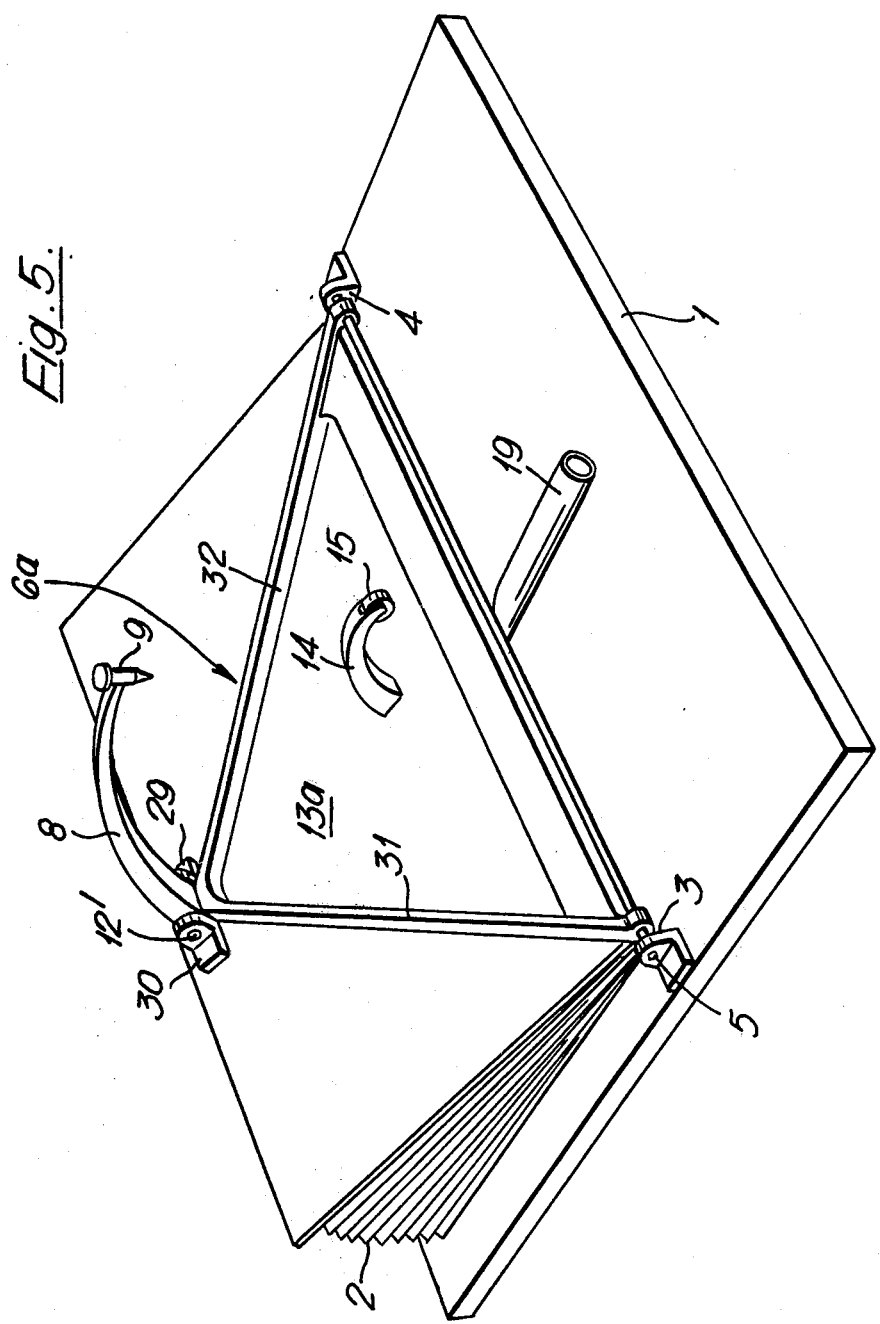

SPIROMETERS

SUMMARY OF THE INVENTION

The present invention relates to spirometers.

Spirometers of the type having an inflatable bellows, are in general use as a diagnostic aid. The patient exhales forcibly into the spirometer and the extent of inflation of the bellows is a measure of the total exhalation of the patient since the beginning of the exhalation. Important data are obtainable from the pattern of the exhalation and for this purpose provision may be made for recording the instantaneous total volume of exhalation against time, normally in the form of a plot on a chart as in the apparatus described in U.S. Pat. No. 3,363,260. It is a difficult matter to provide a bellows which inflates in a uniform manner to provide a non-distorted record and it is necessary, in practice, to adjust each spirometer individually to correct irregularities. This involves supplying the bellows with measured amounts of air and adjusting to provide satisfactorily correct indicated volumes over the total range. Adjustments may be made by moving the bellows bodily with some designs, and/or by adding stiffeners in the form of wires or strips of stainless steel to the gussets to reduce the flexibility of the accordian pleats.

In accordance with the present invention, there is provided a spirometer having an inflatable bellows, a member movable progressively by progressive inflation of the bellows and means providing a track which is engaged by and followed by the movable member during the progressive movement thereof, said track being so adjustable in its configuration as to provide locally adjustable opposition to movement of the movable member.

With a spirometer according to the invention, adjustment for the purpose aforesaid is accomplished in a simple and convenient manner.

Where, as is preferred, the bellows is of the wedge-type, the movable member may be mounted to be moved in an arcuate course by the progressive inflation, and the means providing the track arranged to provide said locally variable opposition by forcing the movable member to deviate locally from said arcuate course.

According to a preferred arrangement, the means providing the track has a set of track adjustment devices positioned along the course of the track, each one of said devices being so mounted as to be moved in a direction across the course of the track. In one preferred construction, the track is provided by a set of components each of which has a track-defining part, said track-defining parts cooperating together to provide the track, and said components being mounted for adjustment of their positions relative to one another to adjust the configuration of the track. Although the number of track-defining parts is finite, in practice limited for example to from 5 to 12, and the configuration of the track not therefore continuously adjustable along its length, satisfactory results are nevertheless obtained in practice.

Conveniently, the said components have linear axes, and are mounted for movement along their linear axes to provide said adjustment and the track-defining parts are faces oriented across said axes.

In a modified arrangement the means providing the track is a track assembly provided in the form of a set of adjustable stops and a facing of resilient material for bridging the stops at least locally when engaged by the movable member thereby reducing such discontinuities in locally variable opposition as would be presented by the stops alone. With this arrangement the stops are not, by themselves, required to provide the track as with the track-defining parts aforesaid and the configuration of the track has less evident discontinuities than that of a track provided by faces of a set of components.

A further advantage of the modified arrangement is that the resilient material provides an uninterrupted surface for engagement by the movable member. It is not therefore necessary for the stops to be formed to occupy their associated segments of the track without leaving spaces which would materially interfere with the traverse of the movable member. A simple construction in which the stops are spaced apart along the direction of the track gives satisfactory results, and in a preferred arrangement these spaced-apart stops are carried by a mounting with which they are threadably engaged and are formed with ends for abutment by the flexible material.

In most designs, the track presents a working surface which is concave along the direction of travel of the movable member. Simplicity of construction, especially as regards the mounting of the facing is obtainable by securing the facing at two positions substantially at or beyond the ends of the track, the length of the material between the two positions being such that it contacts the stops as required. A facing formed to a permanent set may be employed but this is not necessary for most track configurations. A synthetic resinous or other material suitable in its physical properties and dimensions for forming the facing can be readily chosen by those skilled in the art, if necessary after simple experiment.

When desired an arrangement may be adopted in which the resilient material is secured to the stops. This complication is however unnecessary. Indeed the resilient material may have a rest-configuration in which it is spaced apart from at least some of the stops and brought into engagement therewith progressively by the movable member as the member moves along the track.

An essential part of a spirometer is an inflation signal generator responsive to movement of the bellows. This signal generator may simply be a stylus for tracing a performance curve or may be a transducer providing an electrical signal.

The movable member may be mounted for movement with the inflation signal generator so that the movement of the generator through any particular position is directly opposed or opposable by a corresponding part of the track. In a more preferred arrangement, however, the movable member is mounted upon, or otherwise arranged to be driven by, a platen which bears upon the bellows for movement thereby and the spirometer has an inflation signal generator (eg. a stylus for tracing on a sensitive chart) responsive to movement of an inflation sensor. With this arrangement it is the response of the bellows to inflation, rather than the response of the signal generator itself, which is controlled by the configuration of the track. It is found that substantially improved results, in the sense that changes produced by local adjustment of the track are rendered less apparent, are obtained.

A simple and effective arrangement is to have the platen hingedly connected with the inflation sensor, as for example when the movement sensor substantially covers the bellows and is formed with an aperture to the periphery of which the inflation sensor is hingedly connected.

BRIEF DESCRIPTION OF THE DRAWINGS

In the accompanying drawings

FIG. 5 shows part of a third embodiment in perspective.

DESCRIPTION OF THE PREFERRED EMBODIMENTS

Figure 1:
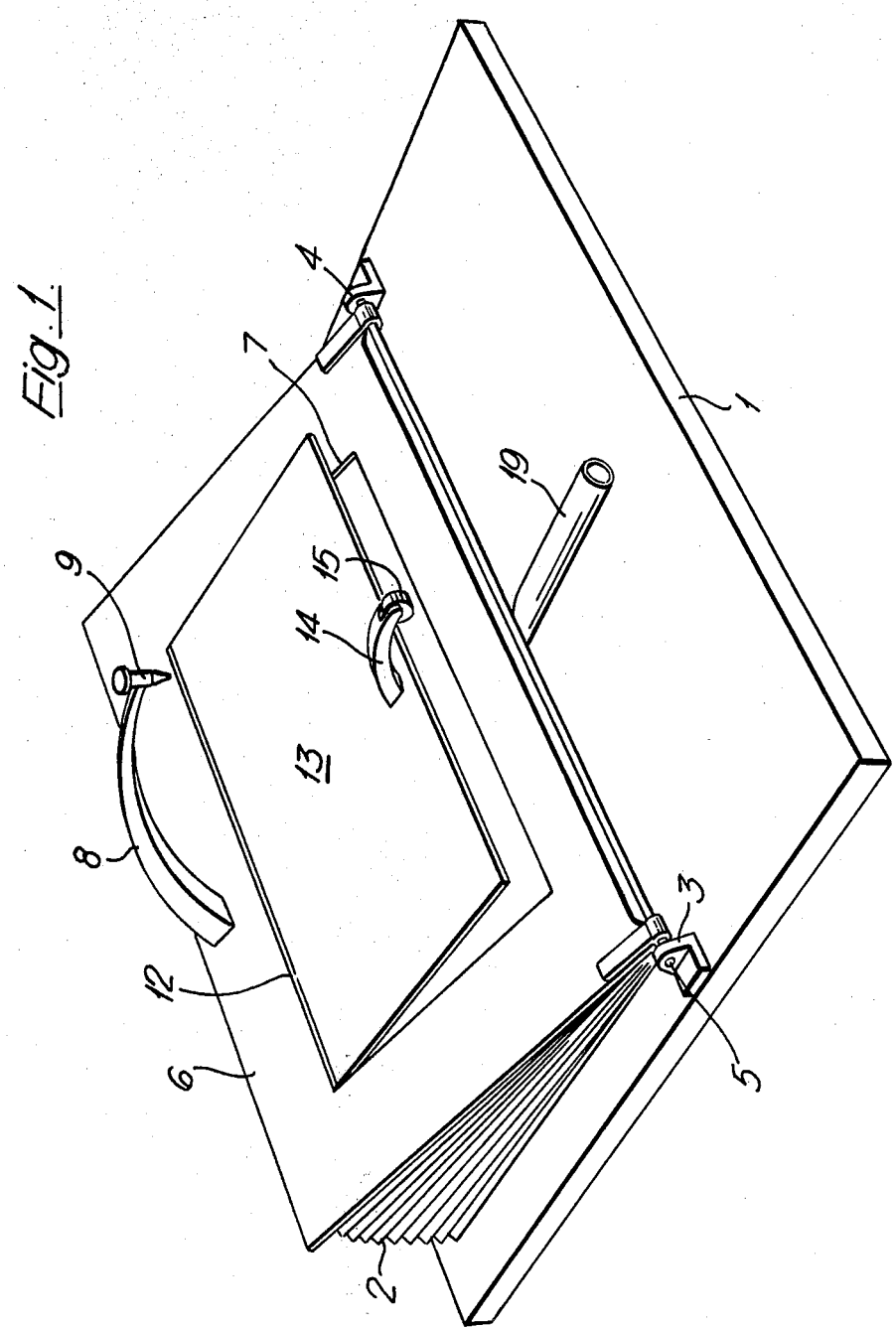
FIG. 1 shows a part of a first embodiment of apparatus according to the invention in perspective.
Figure 2:
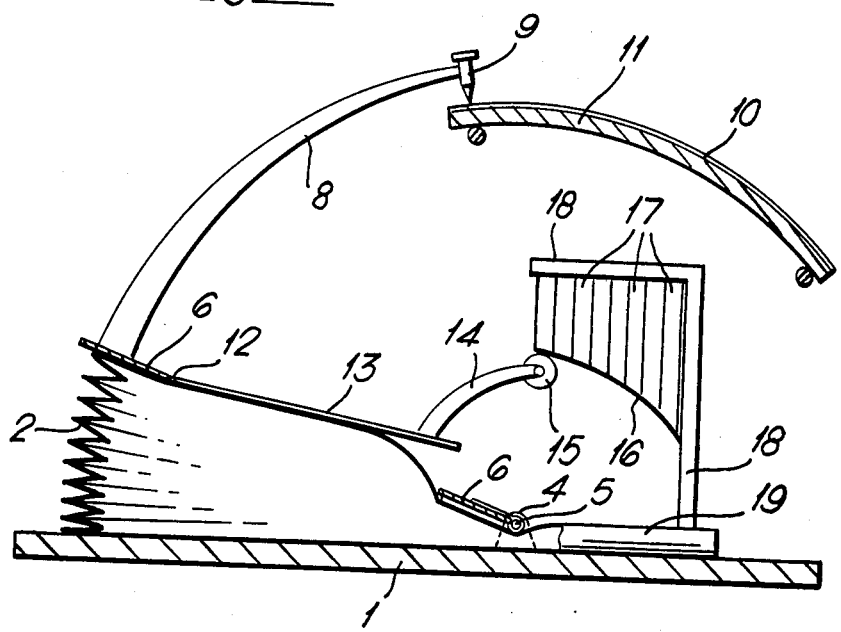
FIG. 2 shows the part of FIG. 1 mounted with other essential parts of the embodiment.

In FIG. 1 of the drawings is shown a base 1 upon which is seated a bellows 2 of the wedge-type. Overlying the bellows, and mounted on the base at 3 & 4 for pivotal movement about axis 5, which lies adjacent to the apex of the bellows, is a rectangular plate 6 formed with large rectangular aperture 7. An arm 8 mounted upon plate 6 carries a stylus 9 for marking a trace upon a chart 10 carried by a chart-carrier 11 (FIG. 2). Chart-carrier 11 is mounted for movement perpendicular to the plane of the paper as described in our U.S. Pat. No. 3,363,260.

To the side 12 of the rectangular aperture, adjacent to arm 8 is hinged a rectangular platen 13. Upon platen 13 is mounted an arm 14 terminating in a roller 15 which engages a track 16 constituted by the ends of a set of elements 17 carried by a bracket 18. As will be seen from FIG. 2 the said ends of elements 17 are sloped at progressively changing angles.

When the bellows is inflated via air inlet 19, stylus 9 is moved for marking chart 10, and roller 15 moves along track 16.

To adjust the apparatus as a final step in its manufacture, the bellows is inflated stepwise, by introducing a series of equal portions of air from a metering device such as a syringe. This causes the stylus to move clockwise, as seen in FIG. 2 and also causes roller 15 to traverse the track 16. The position of the stylus after the introduction of each portion of air is adjusted by moving axially that of the elements 17 which is in contact with the roller. In this way, the pressure of air within the bellows 2 is varied by varying the reaction between platen 13 and the bellows 2. The adjustment of the position of the stylus is dependent only upon the adjustment of that of the elements 17 involved for the particular position of roller 15.

With previously known arrangements, an adjustment has tended to interfere with adjustments previously made for previous positions of the stylus and satisfactory overall adjustment has been a time-consuming operation involving acquired skill.

Figure 3:
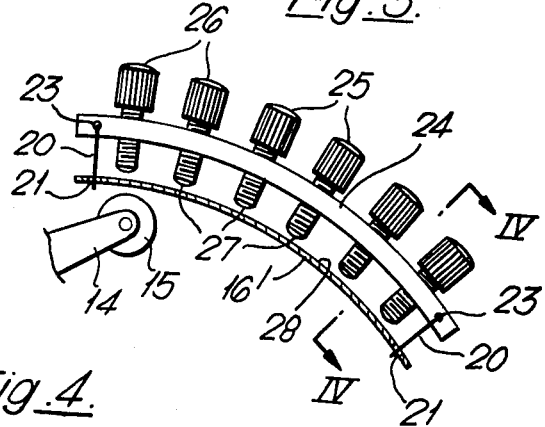
FIG. 3 shows the track assembly and associated movable member of a second embodiment in side elevation.
Figure 4:
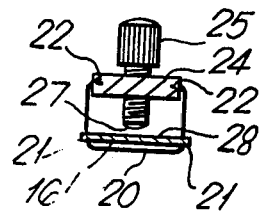
FIG. 4 is a cross section taken at IV—IV of FIG. 3.

The track assembly of FIGS. 3 and 4 is part of a spirometer which is otherwise similar to that shown in FIGS. 1 and 2 of our said prior specification. Instead of having a track 16 constituted by the ends of elements 17 as described therein, the spirometer has a track for the roller 15 presented by the concave face of a strip 16' of resilient synthetic resinous material curved as shown to approximate to the locus of roller 15. Strip 16' is carried at its ends by wire hangers 20 which engage notches formed in the strip at 21 and have their ends 22 inturned and engaged within recesses 23 of curved mounting bar 24. The length of the strip between the notches is greater than the distance between the ends 22 of the hangers by such an amount as to provide the curvature.

Bar 24 is formed at equidistant positions along its length with tapped holes within which are threadably engaged stops 25. Each stop has a knurled head 26 for adjustment purposes and is formed with a smoothly convex end 27 for bearing upon face 28 of the strip 16'.

To adjust the spirometer as a final stop in its manufacture, the bellows is inflated stepwise as previously described and the stops 25 are adjusted in their turn.

With the spirometer in use, the strip 16' is pressed into contact with the ends 27 of stops. It is not necessary that all of the ends 27 should engage the strip simultaneously. The roller 15 may, when between a pair of stops, press the strip into contact only with that pair. In such a case the remainder of the strip, ie. the part or parts beyond the pair of stops may be spaced away from the remaining stops. Alternatively stated, the length of the strip between the notches need not be identical with the length of the track traversed by the roller.

As the roller 15 passes along the track it bears against the strip 16' which effectively bridges the spaces between the stops 25. The essential discontinuity of a finite number of the stops is substantially concealed by the bridging action of the strip 16'.

It will be noted that whereas the embodiment of FIGS. 1 and 2 has eight of the elements 17 (as shown in FIG. 2) an improved result is obtained with only six stop 25.

In the example shown in FIGS. 3 and 4, the strip 16' is formed by cutting from a sheet of low density polyethylene. It has a thickness of 0.7 mm, a width of 7 mm and a length of 100 mm.

The part of the third embodiment shown in FIG. 5 differs from the part of the first embodiment shown in FIG. 1 in that instead of the apertured rectangular plate 6 and the platen 13 there are provided a frame 6a pivotally mounted at 3 and 4 and an enlarged rectangular platen 13a which extends over the whole of the adjacent face of the bellows 2. Brackets 29 and 30 secured to platen 13a are connected to frame 6a for pivotal movement about an axis 12'. Arm 8 is formed as part of frame 6a.

In FIG. 5, platen 13a is shown in its extreme position in contact with frame members 31 and 32. Resistance to the movement of roller 15 produced by the track, causes the platen to pivot out of contact with members 31 and 32.

Roller 15 is arranged to run in engagement with a track in the manner shown in FIGS. 2 and 3. A track constructed as described with reference to FIGS. 3 and 4 is preferred.

It is found that, compared with the arrangement of FIG. 1, the arrangement of FIG. 5 provides a more stable assembly. Additionally, the dynamic characteristics of the apparatus are improved by the reduction of oscillatory movement of the stylus 9.

It is found that, compared with the arrangement of FIG. 1, the arrangement of FIG. 5 provides a more stable assembly. Additionally, the dynamic characteristics of the apparatus are improved by the reduction of oscillatory movement of the stylus 9.

It will be understood that the form of construction described by reference to the drawing is given by way of example only and that various departures may be made therefrom within the scope of the invention claimed.

I claim:

1. A spirometer having an inflatable bellows, inlet means for inflating said bellows, a movable member connected to said bellows having a locus along which said member is drivable progressively by said bellows during progressive inflation thereof, track means positioned, and having a course configured, to be engaged by and followed by said movable member during the progressive driving thereof along said locus and adjusting means for adjusting said configuration of said track means to provide locally adjustable opposition to movement of the movable member and, thereby, to the inflation of said bellows.

2. A spirometer according to claim 1 in which said bellows is of the wedge-type, said movable member is mounted to be moved in an arcuate course by the progressive inflation of said bellows, and said adjusting means includes means to provide said locally adjustable opposition by local variations of said configuration such as to force the movable member to deviate locally from said arcuate course.

3. A spirometer according to claim 2 in which said track means has a set of movable track adjustment devices positioned along the course of the track means, each one of said devices being so mounted as to be moved in a direction across the course of the track means to provide said local variations.

4. A spirometer according to claim 2 in which the track means includes a set of components each one having a track-defining part, said track-defining parts being constructed and arranged to provide the track means, and said components being mounted to permit adjustment of their positions relative to one another to provide said adjustment of configuration.

5. A spirometer according to claim 4 in which said components of said set include linear axes, and said components are mounted with respect to each other to permit movement along said linear axes to provide said adjustment of configuration and said track-defining parts are faces oriented across said axes.

6. A spirometer according to claim 1 in which the track means includes a set of adjustable stops and a facing of resilient material for bridging stops at least locally when said facing is engaged by said movable member, thereby reducing such discontinuities in said locally variable opposition as would be presented by the stops alone.

7. A spirometer according to claim 6 in which said stops are spaced apart along the course of said track means.

8. A spirometer according to claim 7 having a mounting formed with threaded formations, said stops being threadably engaged with said mounting and being formed with ends for abutment by said resilient material.

9. A spirometer according to claim 6 in which the facing has a permanent set by which it is held in proximity to the stops.

10. A spirometer having an inflatable bellows, inlet means for inflating said bellows, a movement sensor connected to said bellows, a platen mounted to bear upon said bellows for progressive movement by said bellows during progressive inflation thereof, means connected with said platen and having a locus along which said means is drivable progressively by said platen, track means positioned, and having a course configured, to be engaged by and followed by said means during the progressive driving thereof along said locus and adjusting means for adjusting said configuration of said track means to provide locally adjustable opposition to movement of the means and, thereby, to the inflation of said bellows.

11. A spirometer according to claim 10 in which the platen is hingedly connected with the movement sensor.

12. A spirometer according to claim 11 in which the movement sensor substantially covers the bellows and is formed with an aperture to the periphery of which the platen is hingedly connected.

13. A spirometer according to claim 11 in which the movement sensor is a frame which extends across the bellows from a pivotal axis and the platen is positioned between the frame and the bellows.

* * * * *